US00PP11449P

United States Patent [19]

Layne

[11] Patent Number: Plant 11,449

[45] Date of Patent: Jul. 18, 2000

[54] 'AC HARROW DAWN' PEACH

[75] Inventor: Richard E. C. Layne, Ontario, Canada

[73] Assignee: Agriculture and Agri-Food Canada, Ontario, Canada

[21] Appl. No.: 09/025,378

[22] Filed: Feb. 18, 1998

[51] Int. Cl.[7] ..... A02H 5/00

[52] U.S. Cl. ..... Plt./197

[58] Field of Search ..... Plt./198, 197

[56] References Cited

U.S. PATENT DOCUMENTS

P.P. 7,066 12/1989 Bradford et al. ..... Plt./198
P.P. 10,548 8/1998 Bjorge et al. ..... Plt./198

OTHER PUBLICATIONS

Dr. Bill Shane, "Fresh Market Peach Varieties for Cooler Climates", Compact Fruit Tree, vol. 30, pp. 89–91, Feb. 22, 1997.

Sharon Hill, "Scientist Peachy Keen on New Fruit Varieties", Windsor Star, p. B1, Feb. 5, 1996.

*Primary Examiner*—Howard J. Locker
*Assistant Examiner*—Wendy A Baker
*Attorney, Agent, or Firm*—Flynn, Thiel, Boutell & Tanis, P.C.

[57] ABSTRACT

A new and distinct variety of peach tree, which has been given the designation 'AC Harrow Dawn', that is cold hardy, disease resistant, productive and bears an attractively colored fruit of good size and quality that is suitable for long distance shipping.

2 Drawing Sheets

FIELD OF THE INVENTION

The present invention relates to a peach variety and more specifically to a peach variety that is cold hardy and disease resistant bearing a high-quality, early season peach for the fresh market.

BACKGROUND OF THE INVENTION

AC Harrow Dawn is a fresh market peach which is distinguished in characteristics from the varieties similar to it, 'Garnet Beauty', 'Harbelle', 'Harson' and 'Harrow Diamond'. 'Garnet Beauty' is the variety it most closely resembles. 'AC Harrow Dawn' has been described by Richard E.C. Layne, HortScience, Vol. 31(6): 1046–1047, October 1996.

'AC Harrow Dawn' peach (*Prunus persica* (L.) Batsch) was released for the Ontario fresh market in 1996 following application for Plant Breeding Rights in Canada on Oct. 11, 1995 (Application Number: 95-645). It is an early season peach that ripens 14 days before 'Redhaven', is cold hardy and disease resistant, productive, bears very attractively colored fruit of good size and quality, and is suitable for long-distance shipping. This variety was recommended for commercial introduction in Canada by members of the Western Ontario Fruit Testing Association (WOFTA) on the basis of generally favorable performance in regional trials in southern Ontario coordinated by WOFTA. 'AC Harrow Dawn' should be adapted to northern regions where Redhaven is successfully grown. To Applicant's knowledge, none of the prior art varieties referred to herein are patented.

SUMMARY OF THE INVENTION

The new and distinct peach variety, which has been given the designation of 'AC Harrow Dawn', produces a high quality early season peach. It is stable and uniform through succeeding asexual propagation. Its fruit ripens just before 'Garnet Beauty' and has a higher proportion of anthocyanin on the skin than the reference varieties it was compared to. 'AC Harrow Dawn' has more than two kidney-shaped nectaries on the petiole while the reference varieties have two nectaries. It flowers later and for a longer duration than the reference varieties.

DETAILED DESCRIPTION OF THE INVENTION

Figure 1:
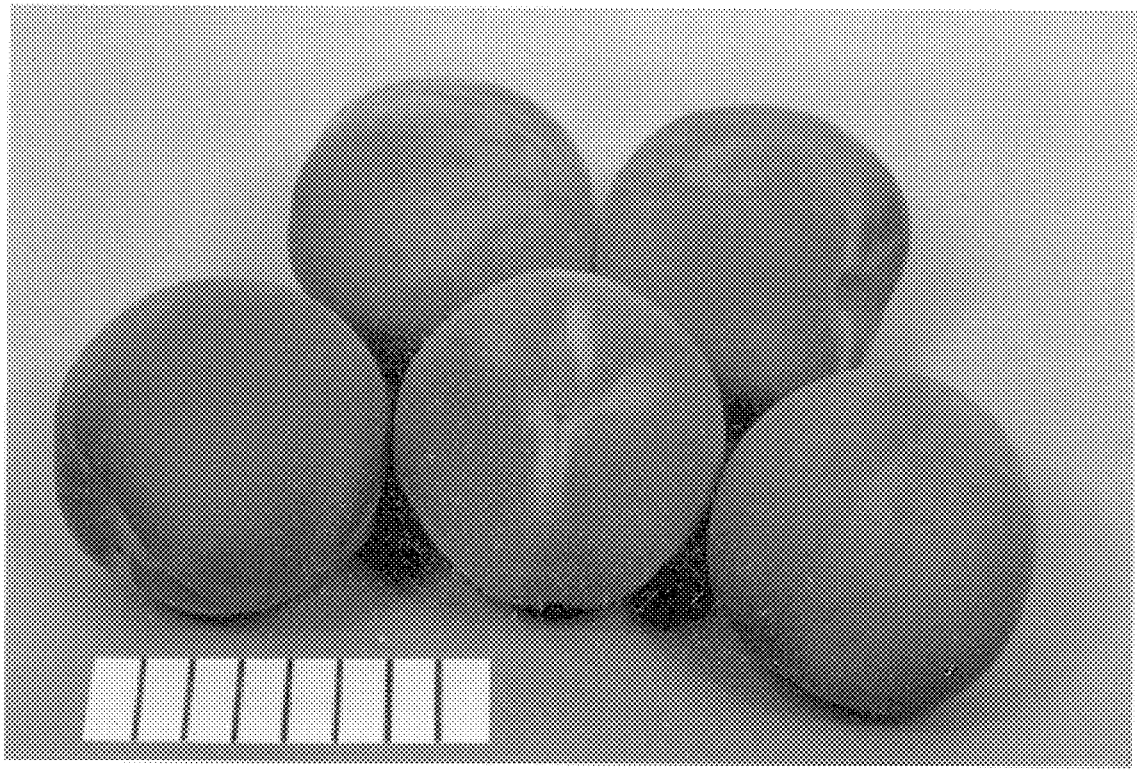
FIG. 1 is a photographic illustration of the whole fruit of 'AC Harrow Dawn' peach.
Figure 2:
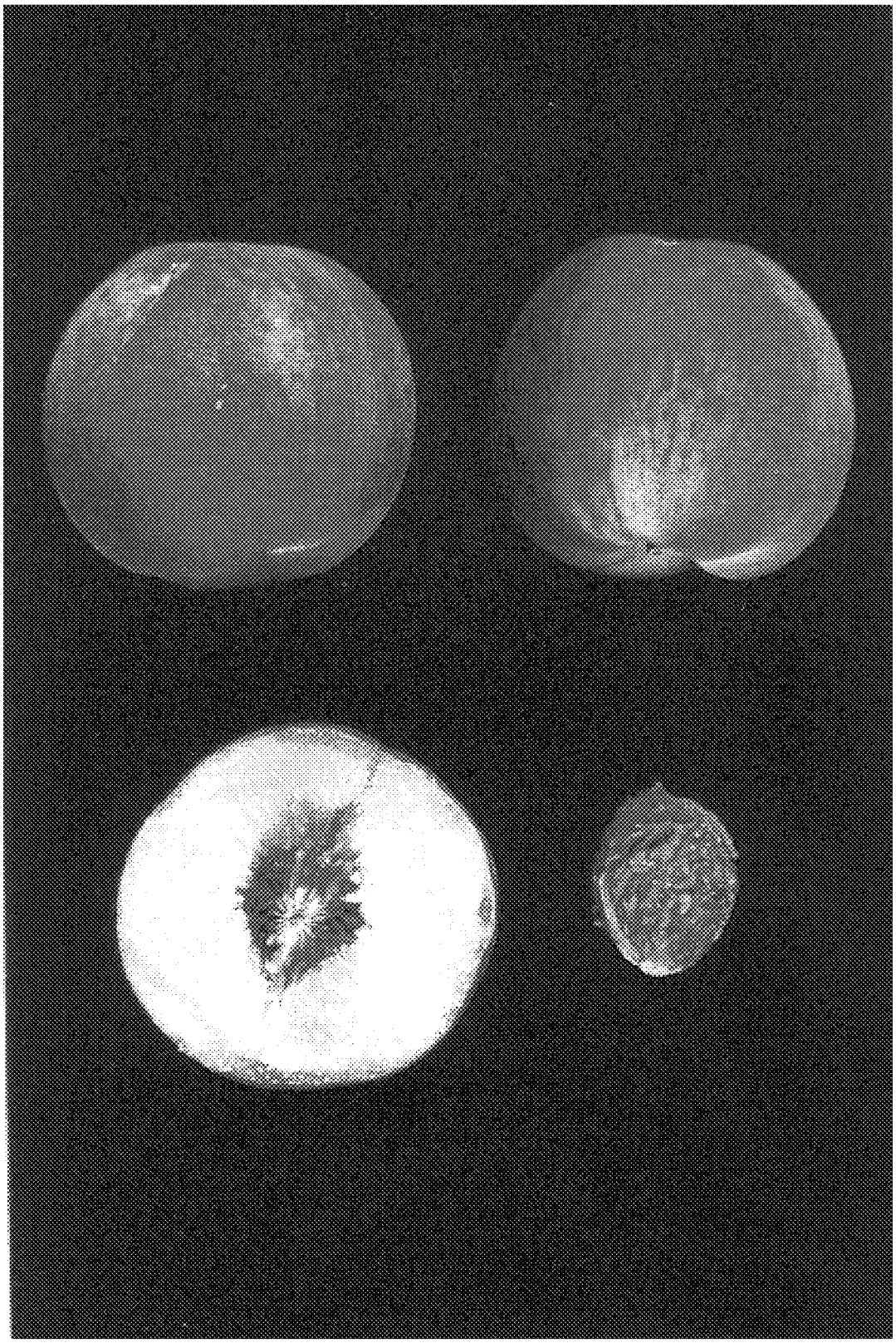
FIG. 2 is a photographic illustration of the whole fruit, bisected fruit and the stone. The color of the flesh, stone and stone cavity are illustrated.

'AC Harrow Dawn' originated at the Agriculture and Agri-Food Canada research station in Harrow, Ontario from a controlled cross of 'Cresthaven'×'Harbinger'. Selected and tested as a seedling hybrid, 'AC Harrow Dawn' was then asexually propagated by budding on peach seedling rootstocks in Harrow, Ontario and tested as HW254 in regional trials coordinated by WOFTA. The asexual propagation demonstrates that such reproduction of the characteristics of the tree are consistent and are established and transmitted through succeeding generations. The tree of this variety is self- pollinated. The color terminology is in accordance with The Royal Horticultural Society Colour Chart.

DESCRIPTION OF VARIETY

'AC Harrow Dawn' is a non-spur type variety with strong vigor compared with 'Harbelle' which has medium vigor. The tree habit is semi-erect, slightly less erect than 'Harrow Diamond' and more erect than the other reference varieties. The tree bark is reddish-brown in color in mid-summer and reddish-brown with a silvery sheen in winter. The leaves are medium in size for 'AC Harrow Dawn' compared with the large size of 'Harrow Diamond' and 'Harson' and medium to large size of 'Garnet Beauty'. The leaf blade is up-folded in profile and the tip is recurved downwards. The angle at the base and tip of the leaf blade is acute. The leaf blade has no anthocyanin and the margins are serrated. The dorsal surface of the leaf is green 141A and the ventral surface is green 138B. The leaf petiole is medium in length for 'AC Harrow Dawn' while 'Harson' is medium to long and 'Harbelle' is short to medium. The petiole has nectaries which are kidney-shaped for 'AC Harrow Dawn' while they are round in shape for 'Harrow Diamond' and 'Harbelle'. 'AC Harrow Dawn' normally has more than two nectaries while the reference varieties have two. There are no leaf stipules present.

The flowering shoot of 'AC Harrow Dawn' has medium anthocyanin while 'Harrow Diamond' has weak anthocyanin. The density of flower buds is high for 'AC Harrow Dawn', medium to high for 'Harson' and medium for 'Harbelle'. The flower buds are in groups of two or more for 'AC Harrow Dawn' while they are isolated for 'Harbelle'. The time of beginning of flowering is medium to late for 'AC Harrow Dawn' while it is medium for the reference varieties. Flower shape is campanulate for 'AC Harrow Dawn' and rosaceous for 'Harrow Diamond'. The calyx is reddish-brown in color. The shape of the petals is elongated for 'AC Harrow Dawn' while it is rounded for 'Harrow Diamond'. 'AC Harrow Dawn' has small sized petals while 'Harrow Diamond' has large petals and 'Harson' has medium sized petals. The petals are medium pink in color for 'AC Harrow Dawn' and light pink for 'Harrow Diamond'. Petal striping is absent and there are five petals per flower. The length of the stamens compared to the petals is longer for 'AC Harrow Dawn', shorter for 'Harrow Diamond' and equal for 'Harson' and 'Harbelle'. There is one pistil and the stigma is positioned at the same level as the anthers. The anthers have pollen present and the ovary is pubescent. The duration of flowering is long for 'AC Harrow Dawn' and medium for the reference varieties.

The fruit matures early to mid-season for 'AC Harrow Dawn' while 'Harrow Diamond' fruit matures slightly earlier and 'Harson' fruit slightly later. The tendency to natural falling of fruit is absent or very weak for 'AC Harrow Dawn' and very weak for 'Garnet Beauty'. Fruit size is medium to large for 'AC Harrow Dawn', medium for 'Harrow Diamond' and large for 'Harson' and 'Harbelle'. The shape of the fruit in profile view is oblong for 'AC Harrow Dawn' and rounded for 'Harrow Diamond', 'Harson' and 'Harbelle'. The shape of the fruit tip is dimpled and the symmetry along the suture is symmetric except for 'Garnet Beauty' which is asymmetric. The prominence of the suture is medium for 'AC Harrow Dawn', low for 'Harrow Diamond', 'Harson' and 'Harbelle'. The depth of the stem cavity is deep for 'AC Harrow Dawn', medium for 'Harrow Diamond' and 'Harbelle' and medium to deep for 'Harson'. The width of the stem cavity is narrow. The ground color of the skin is orange-yellow for 'AC Harrow Dawn', yellow for 'Harrow Diamond' and 'Harson' and cream-yellow for 'Harbelle'. The proportion of fruit skin with anthocyanin coloration is very heavy for 'AC Harrow Dawn', heavy for 'Harrow Diamond', 'Harson' and 'Garnet Beauty' and medium to heavy for 'Harbelle'. 'AC Harrow Dawn' has medium pubescence on the skin while 'Harrow Diamond', 'Harson' and 'Harbelle' have sparse pubescence. The skin is medium to thick for 'AC Harrow Dawn' and medium for the reference varieties. Adherence of the skin to the flesh is weak to medium for 'AC Harrow Dawn', weak for 'Harrow Diamond', strong for 'Harson' and medium for 'Harbelle'. The fruit flesh is firm for 'AC Harrow Dawn', medium to firm for 'Harrow Diamond' and medium for 'Harbelle'. The ground color of the flesh is yellow to orange-yellow and there is no anthocyanin directly under the skin. The fruit flesh of 'AC Harrow Dawn' has anthocyanin present while 'Harbelle' has no anthocyanin. The fruit flesh is not stringy, has a melting texture and intermediate acidity. Juiciness of the flesh is intermediate for 'AC Harrow Dawn' and juicy for 'Harson' and 'Harbelle'.

The size of the stone is medium and the shape is elongated. It has a length of 34.7 mm, a width of 24.7 mm and a thickness of 16.4 mm. The percentage of split or shattered stones is very low for 'AC Harrow Dawn' and slightly higher for 'Harbelle' and 'Garnet Beauty'. 'AC Harrow Dawn' has slight adherence of the stone to the flesh while 'Harbelle' and 'Garnet Beauty' have slightly stronger adherence.

'AC Harrow Dawn' can be distinguished from 'Garnet Beauty', the variety it most closely resembles, by being more erect in tree growth habit than 'Garnet Beauty', having smaller leaves with normally more than two reniform-shaped petiolar glands while 'Garnet Beauty' has normally two. The beginning of flowering of 'AC Harrow Dawn' is a little later and the duration of flowering is also longer than 'Garnet Beauty'. The fruits of 'AC Harrow Dawn' ripen 2 days earlier than 'Garnet Beauty' and have a shorter picking season. The shape of the fruit is symmetric along the suture for 'AC Harrow Dawn' while that for 'Garnet Beauty' is asymmetric. The prominence of the suture is medium for 'AC Harrow Dawn' and high for 'Garnet Beauty'. Anthocyanin coloration of the skin is brighter red for 'AC Harrow Dawn' than for 'Garnet Beauty'. Most of the fruit surface of 'AC Harrow Dawn' is covered with a bright, mostly uniform red blush while with 'Garnet Beauty' the proportion of anthocyanin coloration is ±75% and the blush is less uniform. Adherence of the skin to the flesh is weak to medium for 'AC Harrow Dawn' but strong for 'Garnet Beauty'. The flesh of 'AC Harrow Dawn' is firmer than that of 'Garnet Beauty', and there is no anthocyanin coloration around the stone unlike 'Garnet Beauty' where it is present. The percentage of split or shattered stones is typically lower for 'AC Harrow Dawn' than for 'Garnet Beauty'. The flesh adheres less to the stone for 'AC Harrow Dawn' than for 'Garnet Beauty'. 'AC Harrow Dawn' appears more resistant to canker (Cytospora spp.) and bacterial spot (*Xanthomonas campestris* pv. *pruni*), than 'Garnet Beauty' under natural disease pressure outdoors. 'AC Harrow Dawn' is also more cold hardy than 'Garnet Beauty' in controlled freezing tests.

Additional characteristics of 'AC Harrow Dawn' and the reference varieties are shown in Chart 1 below.

CHART 1

Plant vigor: Average growth (length) of 1 year old shoots.
- *AC Harrow dawn.*—596 mm.
- *Harson.*—376 mm.
- *Harbelle.*—476 mm.
- *Garnet beauty.*—429 mm.
- *Harrow diamond.*—368 mm.

Trunk size/texture: Average trunk size of (circumference) of 4 year old trees:
- *AC Harrow dawn.*—182 mm.
- *Harson.*—205 mm.
- *Harbelle.*—181 mm.
- *Garnet beauty.*—146 mm.
- *Harrow diamond.*—206 mm.

The trunks of all the trees are painted with white latex paint to protect them from sun damage and therefore is very difficult to determine color and texture of the bark on the trunk.

Colors:
- *Fruit skin* (*ground color*).—Yellow, 13A.
- *Fruit skin* (*blush*).—44A.
- *Flesh.*—12A.
- *Pit cavity.*—Dark yellow17A.
- *Pit.*—162A.
- *Leaf* (*dorsal*).—141A.
- *Leaf* (*ventral*).—138B.

Crotch angles: Branch size and crotch angles are controlled by training and pruning methods of the trees. The natural growth habit of the tree is therefore not seen since poorly angled (narrow) branches are pruned out. Remaining branches are approximately 70 degrees from vertical position of the central leader of the tree.

Lenticels: Relative number and size.

*AC Harrow dawn.*—Very few and very small (smaller than 1 mm).

*Harson.*—Moderate number and very small.

*Harbelle.*—Very few and very small.

*Garnet beauty.*—Moderate and very small.

*Harrow diamond.*—Very few and very small.

Avg. bloom date/duration:

*AC Harrow dawn.*—May 3, 4 days duration.

*Harson.*—May 5, 4 days duration.

*Harbelle.*—May 5, 4 days duration.

*Garnet beauty.*—May 5, 4 days duration.

*Harrow diamond.*—May 5, 4 days duration.

Avg. ripe dates/duration:

*AC Harrow dawn.*—July 29, 4 days.

*Harson.*—August 10, 4 days.

*Harbelle.*—August 2, 4 days.

*Garnet beauty.*—August 2, 5 days.

*Harrow diamond.*—July 22, 4 days.

Fruit characteristics:

*AC Harrow dawn.*—Height (mm)=64.6, Width (mm)=64.9, Weight (g)=165.9.

*Harson.*—Height (mm)=68.6, Width (mm)=69.8, Weight (g)=186.8.

*Harbelle.*—Height (mm)=67.5, Width (mm)=68.4, Weight (g)=180.7.

*Garnet beauty.*—Height (mm)=64.0, Width (mm)=64.4, Weight (g)=154.7.

*Harrow diamond.*—Height (mm)=66.8, Width (mm)=65.1, Weight (g)=162.8.

*Garnet beauty.*—9.6.

*Harrow diamond.*—10.7.

Productivity: This is evaluated on a rating system from 1 to 10 where 1 is very little or no crop, 5 is a commercially acceptable amount of fruit on a tree, and 10 represents a crop load so heavy it would break the tree if left un-thinned. All the varieties mentioned for the descriptor having average ratings of 5.

Nectaries:

*AC Harrow dawn.*—Kidney-shaped.

*Harson.*—Kidney shaped.

*Harbelle.*—Round.

*Garnet beauty.*—Kidney-shaped.

*Harrow diamond.*—Round.

Petioles:

*AC harrow dawn.*—Length (mm)=9.5, Width (mm)=1.2.

*Harson.*—Length (mm)=10.9, Width (mm)=1.2.

*Garnet beauty.*—Length (mm)=9.0, Width (mm)=1.3.

*Harbelle.*—Length (mm)=8.4, Width (mm)=1.3.

*Harrow diamond.*—Length (mm)=9.2, Width (mm)=1.3.

PERFORMANCE

Performance of 'AC Harrow Dawn', in comparison with 'Harrow Diamond', 'Harbelle', 'Harson' and 'Garnet Beauty', from 1990 to 1995 is summarized in Table 1. These comparative tests and trials were conducted at the Agriculture and Agri-Food Canada Research Station in Harrow, Ontario. The trial consisted of three replications, in a completely randomized design, with trees spaced 3 meters apart within the row and 5.5 meters between rows.

TABLE 1

Comparison table for 'AC Harrow Dawn'

| CHARACTERISTICS | 'AC HARROW DAWN' | 'HARROW DIAMOND'* | 'HARSON'* | 'HARBELLE'* | 'GARNET BEAUTY'* |
|---|---|---|---|---|---|
| Length of leaf blade | | | | | |
| mean (mm) | 137.6 | 160.5 | 153.1 | 134.1 | 142.6 |
| range | 113–165 | 134–193 | 129–174 | 103–168 | 116–173 |
| standard deviation | 13.9 | 18.8 | 11.5 | 14.5 | 14.5 |
| number measured | 30 | 30 | 30 | 30 | 30 |
| Width of leaf blade | | | | | |
| mean (mm) | 30.7 | 34.1 | 35.9 | 36.0 | 33.3 |
| range | 26–34 | 31–43 | 31–41 | 27–44 | 25–44 |
| standard deviation | 2.1 | 2.5 | 3.1 | 3.8 | 3.0 |
| number measured | 30 | 30 | 30 | 30 | 30 |
| Duration of flowering | long | medium | medium | medium | medium |
| Time of maturity | early to medium | early | medium | early to medium | early to medium |
| Shape of fruit | oblong | rounded | rounded | rounded | oblong |
| Ground color of fruit skin | orange-yellow | yellow | yellow | cream-yellow | orange-yellow |
| Proportion of fruit surface with anthocyanin | very heavy (>75%) | heavy (±75%) | heavy (±75%) | medium to heavy (50–75%) | heavy (±75%) |
| Prominence of fruit suture | medium | low | low | low | high |
| Adherence of fruit skin to flesh | weak to medium | weak | strong | medium | strong |

*reference varieties

Sugar content (brix):

*AC Harrow dawn.*—10.2.

*Harson.*—9.0.

*Harbelle.*—8.5.

I claim:

1. A new and distinct peach tree variety substantially as shown and described herein.

* * * * *